(12) United States Patent
Blasdell et al.

(10) Patent No.: US 10,576,228 B2
(45) Date of Patent: Mar. 3, 2020

(54) INHALATION APPARATUS

(71) Applicant: ACCUTRON, INC., Phoenix, AZ (US)

(72) Inventors: Richard J. Blasdell, Phoenix, AZ (US); Jonathan W. Blasdell, Phoenix, AZ (US)

(73) Assignee: Accutron, Inc., Phoenix, AZ (US)

( * ) Notice: Subject to any disclaimer, the term of this patent is extended or adjusted under 35 U.S.C. 154(b) by 752 days.

(21) Appl. No.: 15/183,529

(22) Filed: Jun. 15, 2016

(65) Prior Publication Data

US 2017/0361057 A1 Dec. 21, 2017

(51) Int. Cl.
*A61M 16/06* (2006.01)
*A61M 16/00* (2006.01)

(52) U.S. Cl.
CPC .......... *A61M 16/009* (2013.01); *A61M 16/06* (2013.01); *A61M 16/0611* (2014.02); *A61M 2202/0208* (2013.01); *A61M 2202/0283* (2013.01)

(58) Field of Classification Search
CPC .......... A61M 16/0611; A61M 16/009
USPC .......... D24/110.4
See application file for complete search history.

(56) References Cited

U.S. PATENT DOCUMENTS

| | | | |
|---|---|---|---|
| 1,206,045 A * | 11/1916 | Smith | A61M 16/06 128/206.24 |
| 1,740,083 A | 12/1929 | Galvin | |
| 2,663,297 A | 12/1953 | Turnburg | |
| 3,393,677 A | 7/1968 | Echard | |
| 3,575,196 A * | 4/1971 | Marrese | A61M 16/009 128/205.24 |
| 3,889,671 A | 6/1975 | Baker | |
| 4,176,666 A | 12/1979 | Hovey | |

(Continued)

FOREIGN PATENT DOCUMENTS

| EM | 003328681-0001 | 9/2017 |
|---|---|---|
| EM | 003328681-0002 | 9/2017 |

(Continued)

OTHER PUBLICATIONS

International Search Report and Written Opinion of the International Searching Authority (ISA/US) dated Jun. 1, 2017 of International Application No. PCT/US2017/021846 filed Oct. 3, 2017.

(Continued)

*Primary Examiner* — Daniel J Colilla
(74) *Attorney, Agent, or Firm* — Sorell, Lenna & Schmidt LLP; William D. Schmidt, Esq.

(57) ABSTRACT

An apparatus for administering a respirable gas to an individual includes a body receivable against a facial area for enclosing a respiratory organ, a vacuum hose, and a scavenger valve. The body is cup shaped, and includes a first side and a second side. An inhalation member extends from the first side of the body. An exhalation member extends from the second side of the body. The vacuum hose is for coupling a vacuum source to the exhalation member. The scavenger valve is coupled to the vacuum hose. The inhalation member is for administering respirable gas into the body, the exhalation member is for exhausting exhaust gas from the body into the vacuum hose, and the scavenger valve is for exhausting exhaust gas therethrough from the vacuum hose to an atmosphere.

10 Claims, 16 Drawing Sheets

(56) References Cited

U.S. PATENT DOCUMENTS

| | | | |
|---|---|---|---|
| 4,219,020 A * | 8/1980 | Czajka | A61M 16/009 128/205.25 |
| 4,248,218 A | 2/1981 | Fischer | |
| 4,265,239 A * | 5/1981 | Fischer, Jr. | A61M 16/009 128/205.17 |
| 4,312,339 A * | 1/1982 | Thompson, Sr. | A61M 16/009 128/205.25 |
| 4,527,558 A | 7/1985 | Hoenig | |
| 4,770,169 A * | 9/1988 | Schmoegner | A61M 16/06 128/206.24 |
| 4,846,170 A | 7/1989 | McAnalley | |
| 4,944,310 A | 7/1990 | Sullivan | |
| 5,018,519 A | 5/1991 | Brown | |
| D321,570 S | 11/1991 | Blasdell | |
| 5,109,839 A * | 5/1992 | Blasdell | A61M 16/06 128/203.12 |
| 5,267,557 A | 12/1993 | Her-Mou | |
| 5,311,862 A | 5/1994 | Blasdell et al. | |
| D353,198 S | 12/1994 | Blasdell et al. | |
| 5,400,781 A | 3/1995 | Davenport | |
| 5,419,317 A | 5/1995 | Blasdell | |
| D365,632 S | 12/1995 | Blasdell | |
| 5,676,133 A | 10/1997 | Hickle et al. | |
| D390,653 S | 2/1998 | Blasdell | |
| D398,987 S | 9/1998 | Cotner et al. | |
| 5,857,460 A | 1/1999 | Poplitz | |
| 6,019,101 A | 2/2000 | Cotner et al. | |
| 6,135,109 A * | 10/2000 | Blasdell | A61M 16/06 128/206.21 |
| 6,263,874 B1 | 7/2001 | Ledez | |
| 7,500,482 B2 | 3/2009 | Biederman | |
| 8,001,968 B2 | 8/2011 | Doty et al. | |
| 8,893,720 B2 | 11/2014 | Cohen | |
| D777,905 S | 1/2017 | Wolf et al. | |
| 9,656,037 B2 | 5/2017 | Guyette | |
| 2003/0145859 A1 | 8/2003 | Bohn | |
| 2010/0132706 A1 * | 6/2010 | Nashed | A61M 16/0078 128/203.28 |
| 2010/0313891 A1 * | 12/2010 | Veliss | A61M 16/06 128/206.26 |
| 2011/0048417 A1 * | 3/2011 | Ahlmen | A61M 16/009 128/202.22 |
| 2011/0240028 A1 * | 10/2011 | Tatarek | A61M 16/009 128/205.27 |
| 2012/0138058 A1 | 6/2012 | Fu et al. | |
| 2012/0285457 A1 | 11/2012 | Mansour et al. | |
| 2013/0109992 A1 * | 5/2013 | Guyette | A61M 16/06 600/532 |
| 2017/0259018 A1 | 9/2017 | Blasdell et al. | |
| 2017/0361057 A1 | 12/2017 | Blasdell et al. | |

FOREIGN PATENT DOCUMENTS

| | | |
|---|---|---|
| EM | 003328681-0003 | 9/2017 |
| EM | 003328681-0004 | 9/2017 |

OTHER PUBLICATIONS

International Search Report and Written Opinion of the International Searching Authority (ISA/US) dated Aug. 11, 2017 of International Application No. PCT/US2017/036987 filed Jun. 12, 2017.

Supplementary European Search Report of the European Patent Office dated Jan. 2, 2020 issued in European No. 17813867.3 (EP3471809) filed Jun. 12, 2017 for Inhalation Apparatus.

* cited by examiner

INHALATION APPARATUS

FIELD OF THE INVENTION

This invention relates to respiratory or inhalation systems and, more particularly, to apparatus for use in the administration of medical and dental gases.

BACKGROUND OF THE INVENTION

Inhalation or respiratory systems for administering respirable gas to an individual are well known. Of particular significance are apparatus employed in the medical and dental arts for dispensing medical and dental gases, such as anesthetic and analgesic gases and oxygen and nitrous oxide, to a patient.

Typically, inhalation systems include a source of a selected pressurized gas and means to deliver the gas to the external respiratory organs of the patient. A breathing device, such as a mask, is fitted to the face of the patient to embrace the nose and/or the mouth. The source, which may be either portable or fixed, usually includes a flow regulator. A delivery conduit, generally in the form of a flexible hose, communicates between the source and the breathing device. Optionally, the system may include scavenging apparatus comprising a return conduit extending from the breathing device to a source of vacuum.

The prior art has devised an array of personal breathing devices in numerous structural configurations. These personal breathing devices, commonly referred to as inhalation masks or facemasks, serve a variety of functions. Known, for example, are masks that extend over the mouth and the nose of the patient while others receive only the nose. Commonly, masks include a fitting for attachment of a gas delivery conduit. In some instances, an exhalation valve is incorporated into the mask to prevent the entrance of ambient air.

In recognition of the concern over collection and disposal of expired gas, skilled artisans have developed a variety of solutions useful with inhalation masks, such as scavenger valve attachments, scavenger hoods useful with inhalation masks, and scavenger circuits. Although these prior art examples initially appeared adequate, structural complexities inherent in the prior art scavenging solutions have proven less than satisfactory, thereby necessitating continued improvement in the art.

SUMMARY OF THE INVENTION

According to the principle of the invention, an apparatus for administering a respirable gas to an individual, which individual includes a facial area containing a respiratory organ for receiving respirable gas and for expelling exhaust gas, and for scavenging exhaust gas from the individual, includes a body, a vacuum hose, and a scavenger valve. The body is cup-shaped, includes a first side and a second side, and is receivable against the facial area for enclosing the respiratory organ. An inhalation member extends from the first side of the body. An exhalation member extends from the second side of the body. The vacuum hose is for coupling a vacuum source to the exhalation member. The scavenger valve is coupled to the vacuum hose. The inhalation member is for administering respirable gas into the body, the exhalation member is for exhausting exhaust gas from the body into the vacuum hose, and the scavenger valve is for exhausting exhaust gas therethrough from the vacuum hose to an atmosphere. The body includes an inner surface that defines an interior of body, the inhalation member is further for administering respirable gas from an inlet of the inhalation member into the interior, and the exhalation member is further for exhausting exhaust gas through an inlet of the exhalation member from the interior to the vacuum hose. A concave surface contour in the inner surface of the body extends from the outlet of the inhalation member to the inlet of the exhalation member. The concave surface contour cooperates with the outlet of the inhalation member to form a laminar flow of respirable gas from the outlet of the inhalation member to the interior, when respirable gas is applied to the interior from the outlet of the inhalation member. The concave surface contour cooperates with the inlet of the exhalation member to form a laminar flow of exhaust gas from the interior to the inlet of the exhalation member, when exhaust gas is exhaled into the interior. The scavenger valve is further for disabling gas flow therethrough into the vacuum hose from the atmosphere.

According to the principle of the invention, an apparatus for administering a respirable gas to an individual, which individual includes a facial area containing a respiratory organ for receiving respirable gas and for expelling exhaust gas, and for scavenging exhaust gas from the individual, includes a body, a vacuum hose, and a scavenger valve. The body is cup-shaped, includes a first side and a second side, and is receivable against the facial area for enclosing the respiratory organ. An inhalation member extends from the first side of the body. An exhalation member extends from the second side of the body. The vacuum hose couples a vacuum source to the exhalation member. The scavenger valve is coupled to the vacuum hose between the exhalation member and the vacuum source. The inhalation member is for administering respirable gas into the body, the exhalation member is for exhausting exhaust gas from the body into the vacuum hose, and the scavenger valve is for exhausting exhaust gas therethrough from the vacuum hose to an atmosphere between the exhalation member and the vacuum source. The body includes an inner surface that defines an interior of body, the inhalation member is further for administering respirable gas from an inlet of the inhalation member into the interior, and the exhalation member is further for exhausting exhaust gas through an inlet of the exhalation member from the interior to the vacuum hose. A concave surface contour in the inner surface of the body extends from the outlet of the inhalation member to the inlet of the exhalation member. The concave surface contour cooperates with the outlet of the inhalation member to form a laminar flow of respirable gas from the outlet of the inhalation member to the interior, when respirable gas is applied to the interior from the outlet of the inhalation member. The concave surface contour cooperates with the inlet of the exhalation member to form a laminar flow of exhaust gas from the interior to the inlet of the exhalation member, when exhaust gas is exhaled into the interior. The scavenger valve is further for disabling gas flow therethrough into the vacuum hose from the atmosphere.

According to the principle of the invention, an apparatus for administering a respirable gas to an individual, which individual includes a facial area containing a respiratory organ for receiving respirable gas and for expelling exhaust gas, and for scavenging exhaust gas from the individual, includes a body, and a respirator circuit. The body is cup-shaped, includes a first side and a second side, and is receivable against the facial area for enclosing the respiratory organ. An inhalation member extends from the first side of the body. An exhalation member extends from the second side of the body. The respirator circuit includes a delivery hose coupling a gas source to the inhalation member, a vacuum hose coupling a vacuum source to the exhalation member, and a scavenger valve coupled to the vacuum hose between the exhalation member and the vacuum source. The delivery hose is for delivering respirable gas from the gas source to the inhalation member, the inhalation member is for administering respirable gas into the body, the exhalation member is for exhausting exhaust gas from the body into the vacuum hose, and the scavenger valve is for exhausting exhaust gas therethrough from the vacuum hose to an atmosphere between the exhalation member and the vacuum source. The body includes an inner surface that defines an interior of body, the inhalation member is further for administering respirable gas from an inlet of the inhalation member into the interior, and the exhalation member is further for exhausting exhaust gas through an inlet of the exhalation member from the interior to the vacuum hose. A concave surface contour in the inner surface of the body extends from the outlet of the inhalation member to the inlet of the exhalation member. The concave surface contour cooperates with the outlet of the inhalation member to form a laminar flow of respirable gas from the outlet of the inhalation member to the interior, when respirable gas is applied to the interior from the outlet of the inhalation member. The concave surface contour cooperates with the inlet of the exhalation member to form a laminar flow of exhaust gas from the interior to the inlet of the exhalation member, when exhaust gas is exhaled into the interior. The scavenger valve is further for disabling gas flow therethrough into the vacuum hose from the atmosphere.

BRIEF DESCRIPTION OF THE DRAWINGS

Referring to the drawings.

DETAILED DESCRIPTION

The present invention provides, among other things, a new and improved inhalation apparatus for administering a respirable gas to an individual, which individual includes a facial area containing a respiratory organ for receiving respirable gas and for expelling exhaust gas, and for scavenging exhaust gas from the individual.

Figure 1:
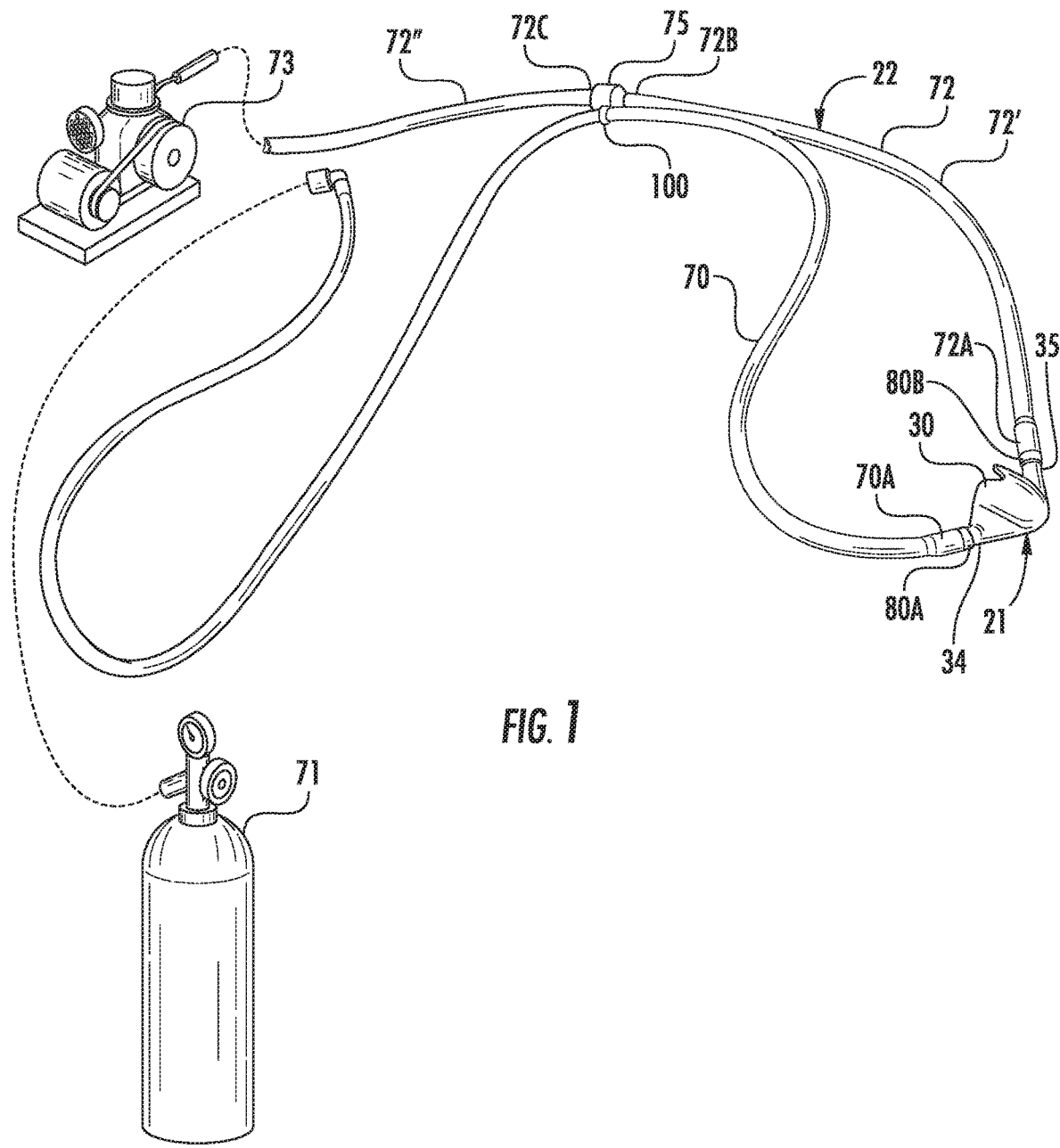
FIG. 1 is a perspective view of an inhalation apparatus for administering a respirable gas to an individual, which individual includes a facial area containing a respiratory organ for receiving respirable gas and for expelling exhaust gas, and for scavenging exhaust gas from the individual, the inhalation apparatus including a mask, and a respirator circuit for delivering respirable gas to the mask and for exhausting exhaust gas from the mask, the respirator circuit including a delivery hose for coupling a gas source to an inhalation member of the mask, a vacuum hose for coupling a vacuum source to an exhalation member of the mask, and a scavenger valve coupled to the vacuum hose for exhausting exhaust gas from the vacuum hose to an atmosphere at a location apart from the mask.

Turning to the drawings, in which like reference characters indicate corresponding elements throughout the several views, attention is first directed to FIG. 1, in which is seen an inhalation apparatus 20 for administering a respirable gas to an individual, which individual includes a facial area containing a respiratory organ for receiving respirable gas and for expelling exhaust gas, and for scavenging exhaust gas from the individual. Inhalation apparatus 20 includes a mask 21, and a respirator circuit 22 for delivering respirable gas to mask 21, for scavenging exhaust gas from mask 21, and for discharging the exhaust gas to an atmosphere at a remote location relative to mask 21.

Referring to FIGS. 5-13 in relevant part, mask 21 includes a body 30. Body 60 is cup shaped, is receivable against the facial area for enclosing the respiratory organ, and is integrally formed. Body 30 includes opposite sides 31 and 32, a frontal midpoint 33 at the front of body 30, inhalation member 34, and exhalation member 35. Inhalation member 34 extends from side 31 of body 30, and exhalation member 35 extends from side 32 of body 30. Body 30 terminates with a rearwardly directed peripheral edge 36. Edge 36 is a terminal portion of body 30 at the rear of body 30. Body 30 further includes outer surface 37, and inner surface 38. Inner surface 38 extends inwardly from edge 36 at the rear of body 30 toward the front of body 30, and bounds interior 40 of body 30 of mask 21. Body 30 is sized to receive the external respiratory organs, specifically the nose, of an individual. Edge 36 is contoured to be received against the facial area surrounding the nose. Interior 40 receives the nose of the individual, when edge 36 is received against the facial area surrounding the nose. Body 30 is molded of a flexible elastic material such as the thermoplastic elastomer found under the exemplary trademark KRATON®. Edge 36 is readily deformable to be pliantly received against the facial area in sealing engagement therewith. Mask 21 can be disposable. However, mask 21 can be reused after suitable cleaning between uses, such as by autoclaving.

Inhalation member 34 is for administering respirable gas into body 30, specifically into interior 40 of body 30, and exhalation member 35 is for exhausting exhaust gas from body 30, specifically from interior 40 of body 21. Inhalation member 34, a conduit, is a cylindrical sidewall 50 having a cylindrical inner surface 50A defining a bore 51 that extends from inlet 52 to outlet 53 to interior 40. Inhalation member 34 projects angularly rearward from side 31 of body 30 from outlet 53, in communication with interior 40, to inlet 52. Exhalation member 35, a conduit, is a cylindrical sidewall 60 having a cylindrical inner surface 60A defining a bore 61 that extends from outlet 62 to inlet 63 to interior 40. Exhalation member 35 projects angularly rearward from side 32 of body 30 from inlet 63, in communication with interior 40, to outlet 62.

Referring to FIG. 1, respirator circuit 22 includes a flexible delivery hose 70 for coupling gas source 71 to inhalation member 34 of mask 21, a flexible vacuum hose 72 for coupling a vacuum source 73 to exhalation member 35 of mask 21, and a scavenger valve 75, coupled to vacuum hose 72 away from mask 21, for exhausting exhaust gas from vacuum hose 72 to an atmosphere away from mask 21 or otherwise at a location that is remote from mask 21. Gas source 71 is for delivering respirable gas to delivery hose 70, delivery hose 70 is for delivering respirable gas from gas source 71 to inhalation member 34, inhalation member 34 is for administering respirable gas applied thereto from delivery hose 70 into body 30, specifically into interior 40 of body 30, exhalation member 35 is for exhausting exhaust gas from body 30, specifically from interior 40 of body 30, into vacuum hose 72, scavenger valve 75 is for exhausting exhaust gas therethrough from vacuum hose 72 to an atmosphere between exhalation member 35 and vacuum source 73 at a location remote from mask 21, and vacuum source is for applying a vacuum to vacuum hose 72 for drawing exhaust gas from body 30, specifically into vacuum hose 72 from interior 40 of body 30 through exhalation member 35.

Figure 2:
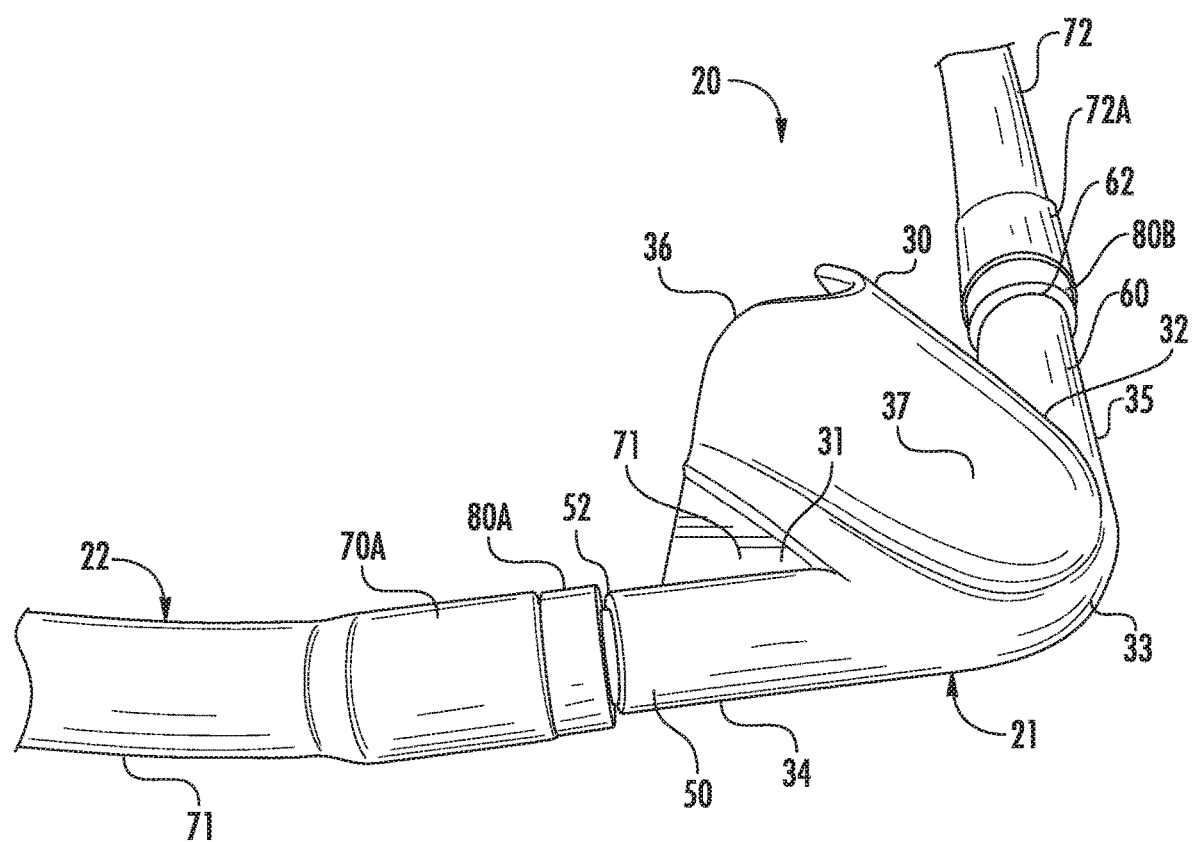
FIGS. 2 and 3 are fragmentary perspective views corresponding to FIG. 1, illustrating the delivery hose coupled to the inhalation member of the mask, and illustrating the vacuum hose coupled to the exhalation member of the mask.
Figure 3:
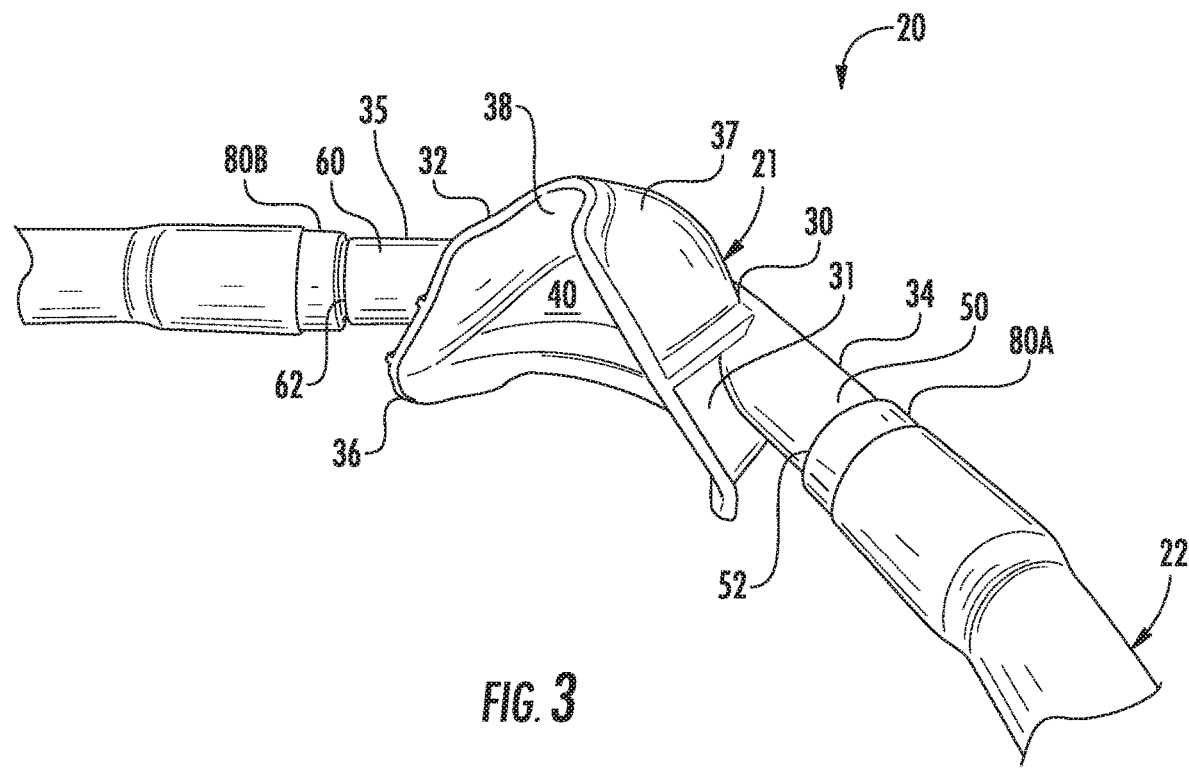

In FIGS. 1, 2, and 3, outlet end 70A of delivery hose 70 is connected to inlet 52 of cylindrical sidewall 50 of inhalation member 34 with one connector 80A, and inlet end 72A of vacuum hose 72 is connected to outlet 62 of cylindrical sidewall 60 of exhalation member 35 with another identical connector 80A. Connector 80A is for admitting respirable gas into inhalation member 34, and connector 80B is for conducting exhaust gas from exhalation member 35.

Figure 4:
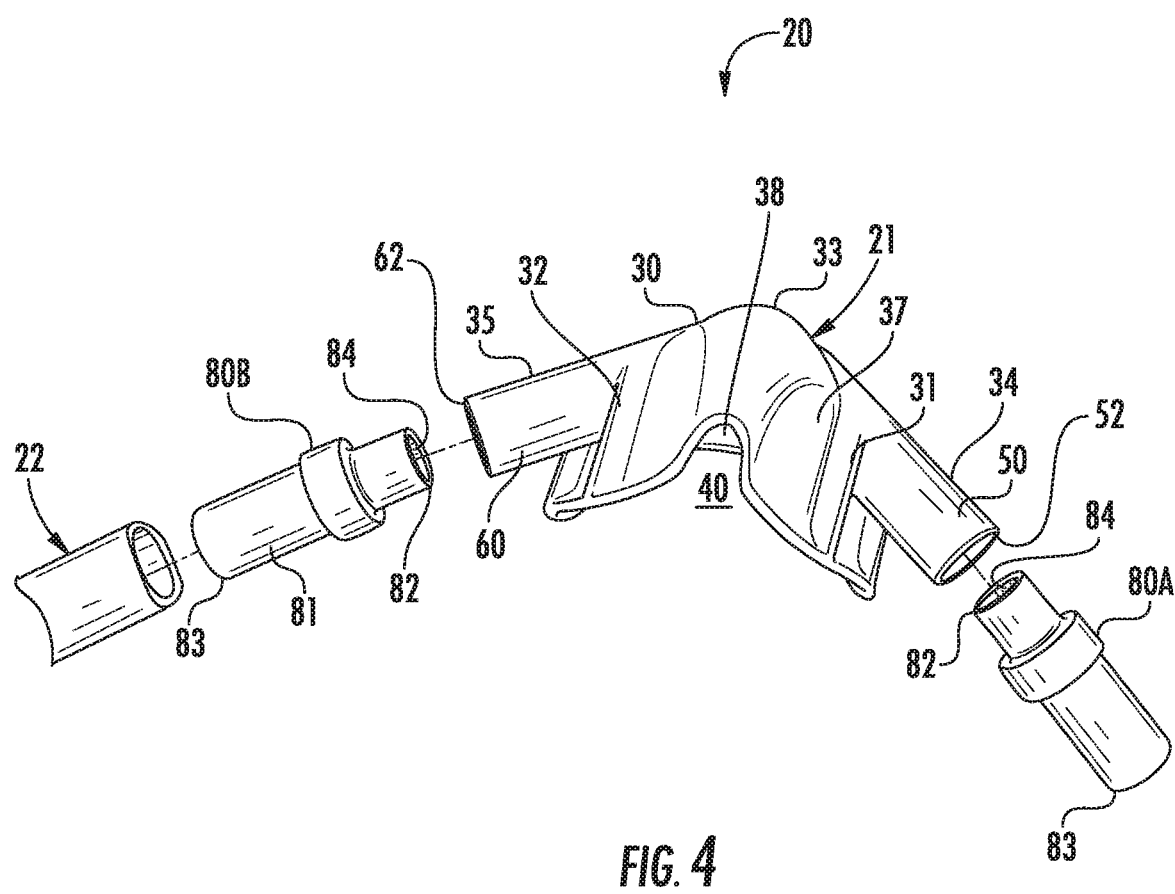
FIG. 4 is a fragmentary exploded view corresponding to FIG. 1, showing adapters for coupling the delivery and vacuum hoses to the inhalation and exhalation members, respectively.
Figure 5:
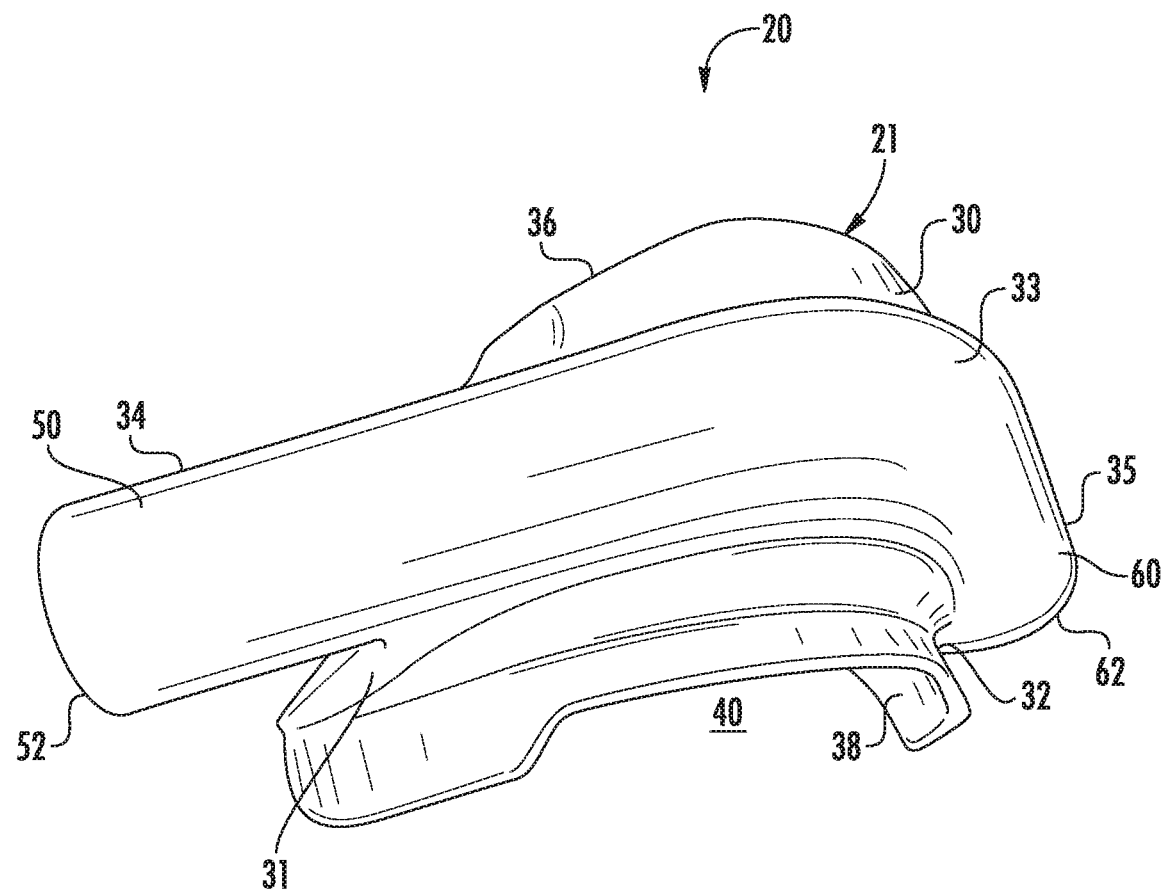
FIGS. 5-13 are perspective views of the mask corresponding to FIG. 1.
Figure 6:
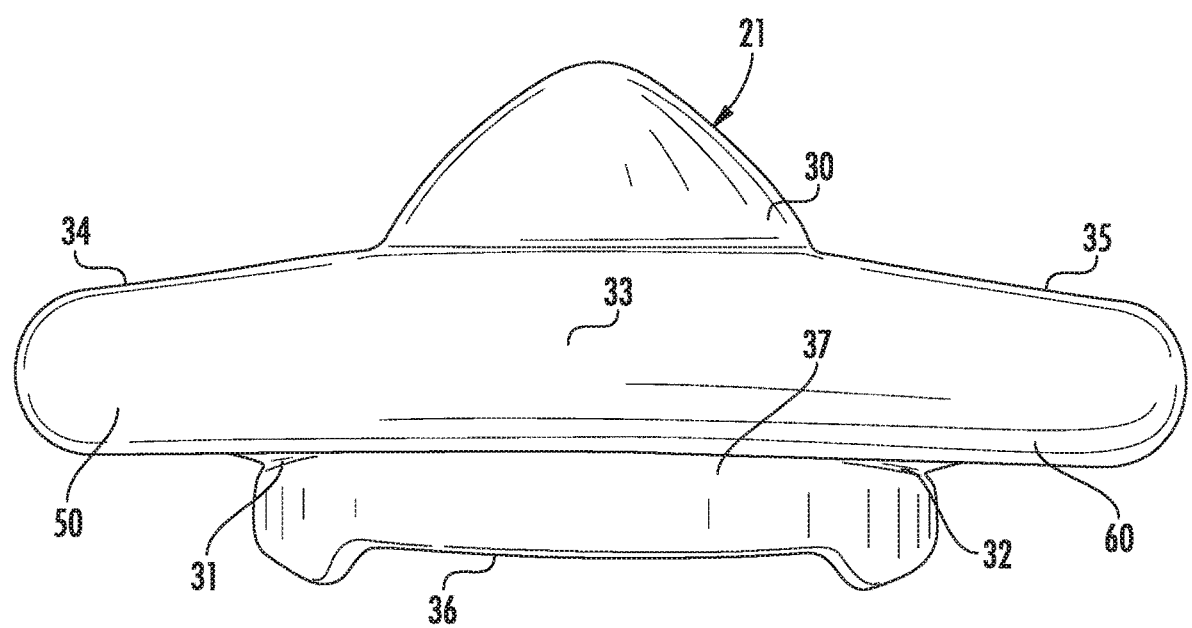
Figure 7:
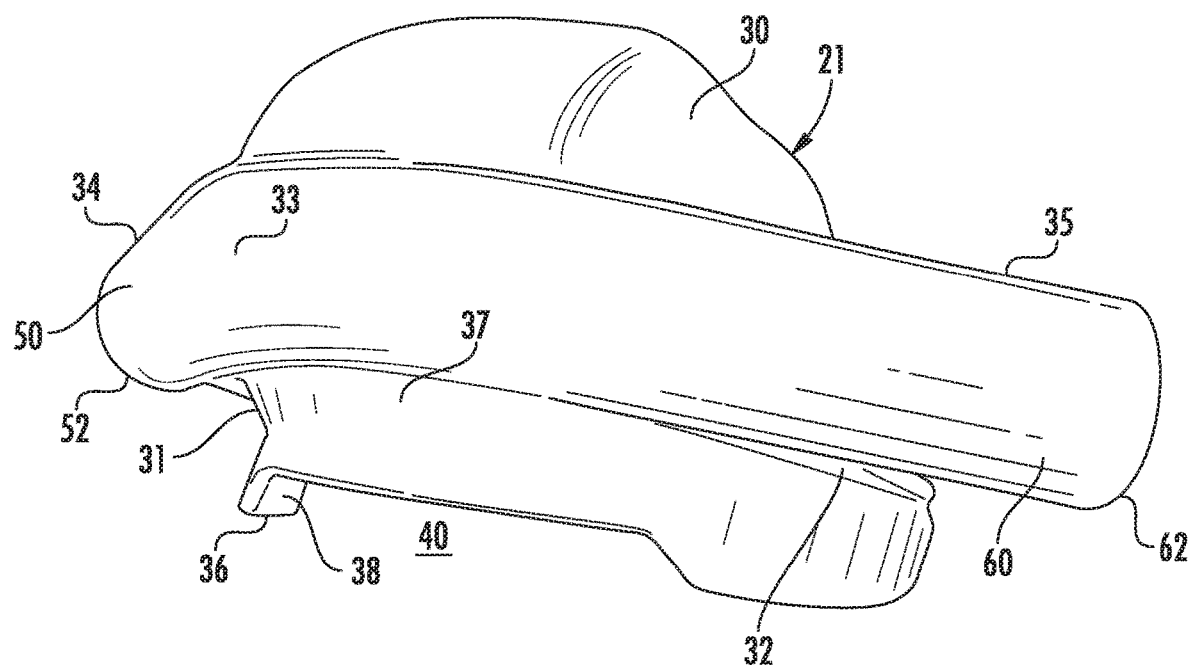
Figure 8:
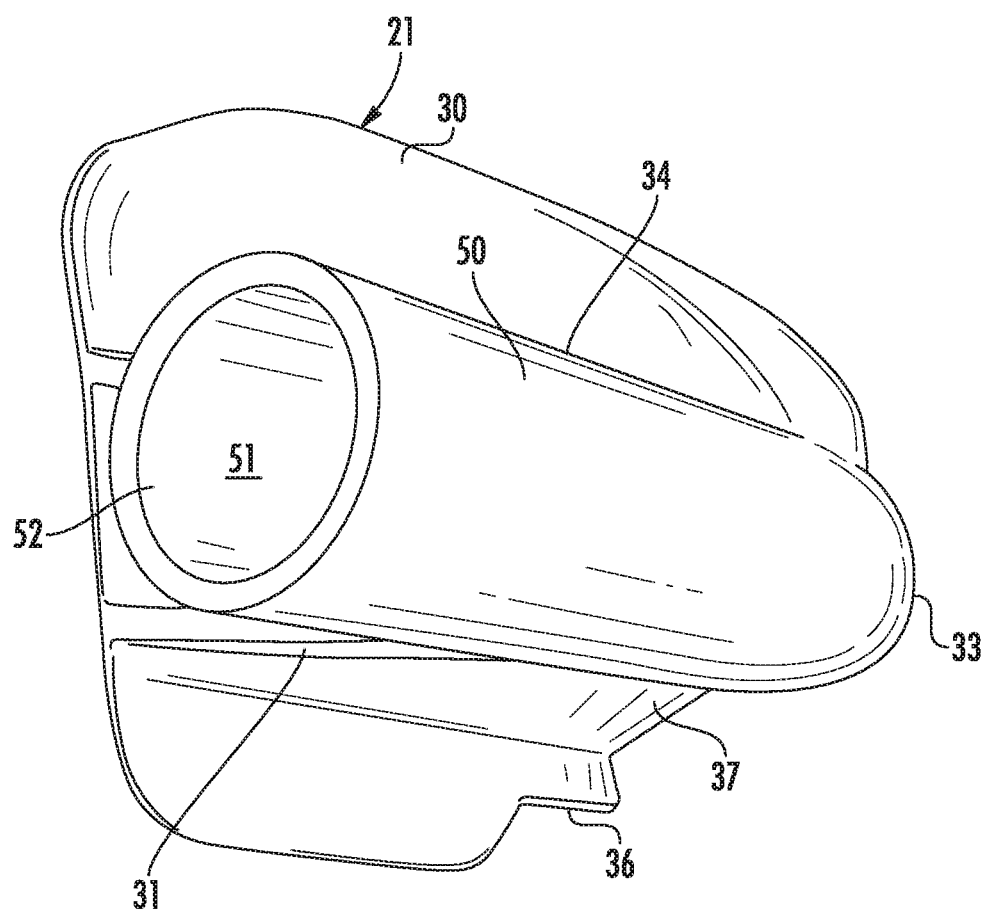
Figure 9:
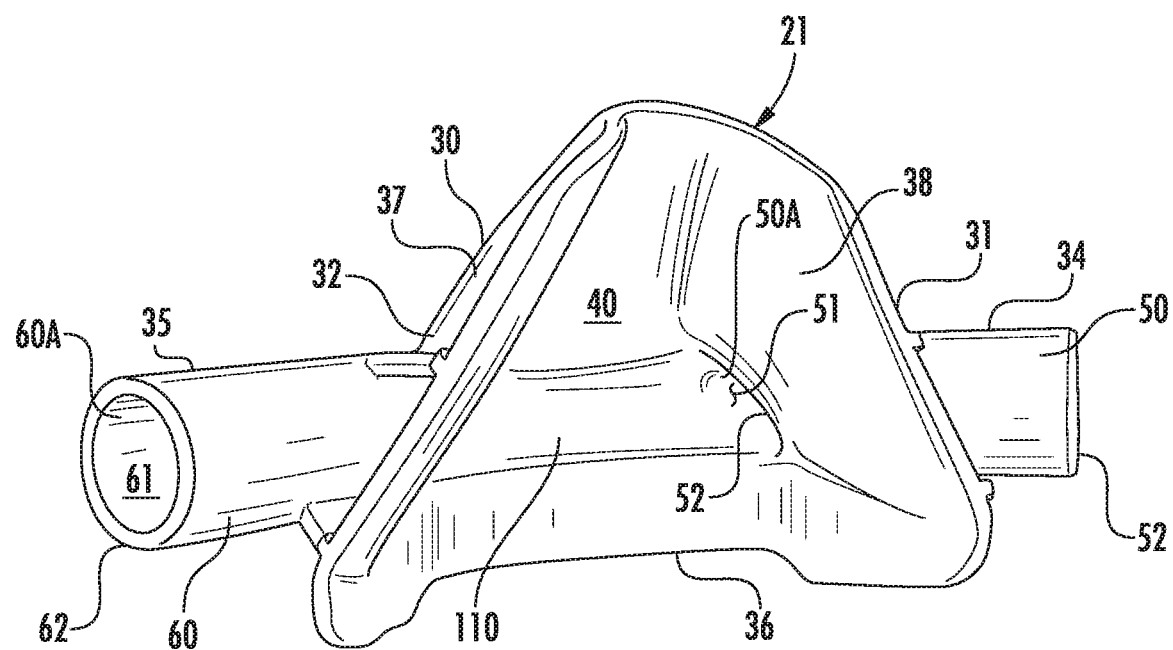
Figure 10:
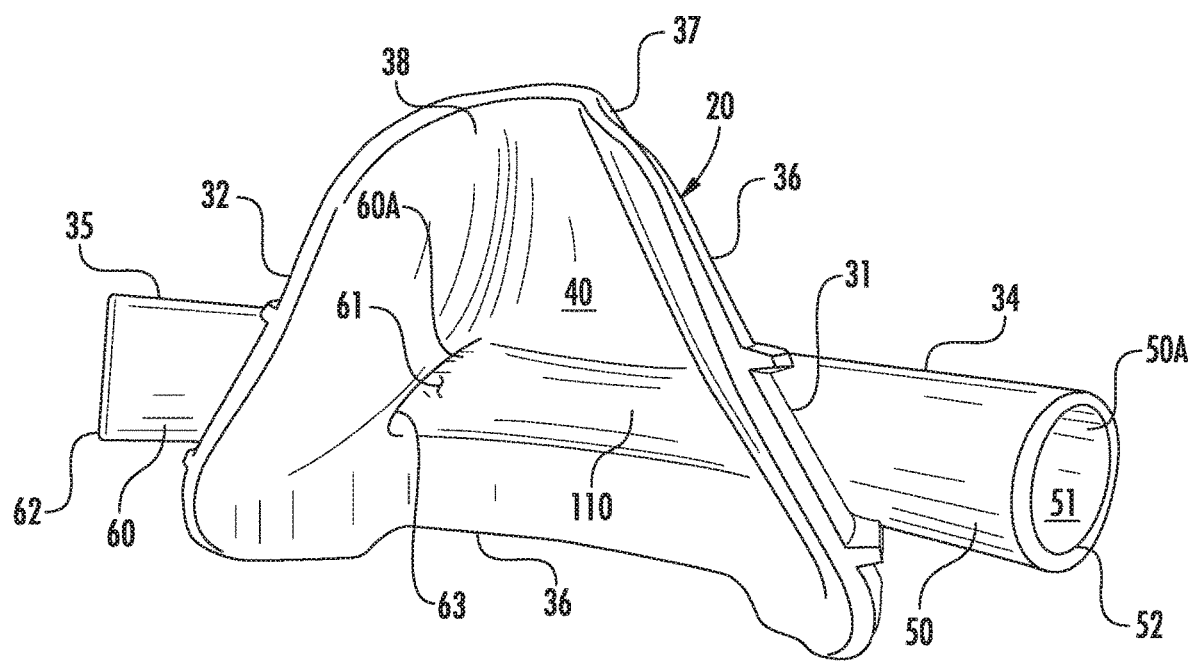
Figure 11:
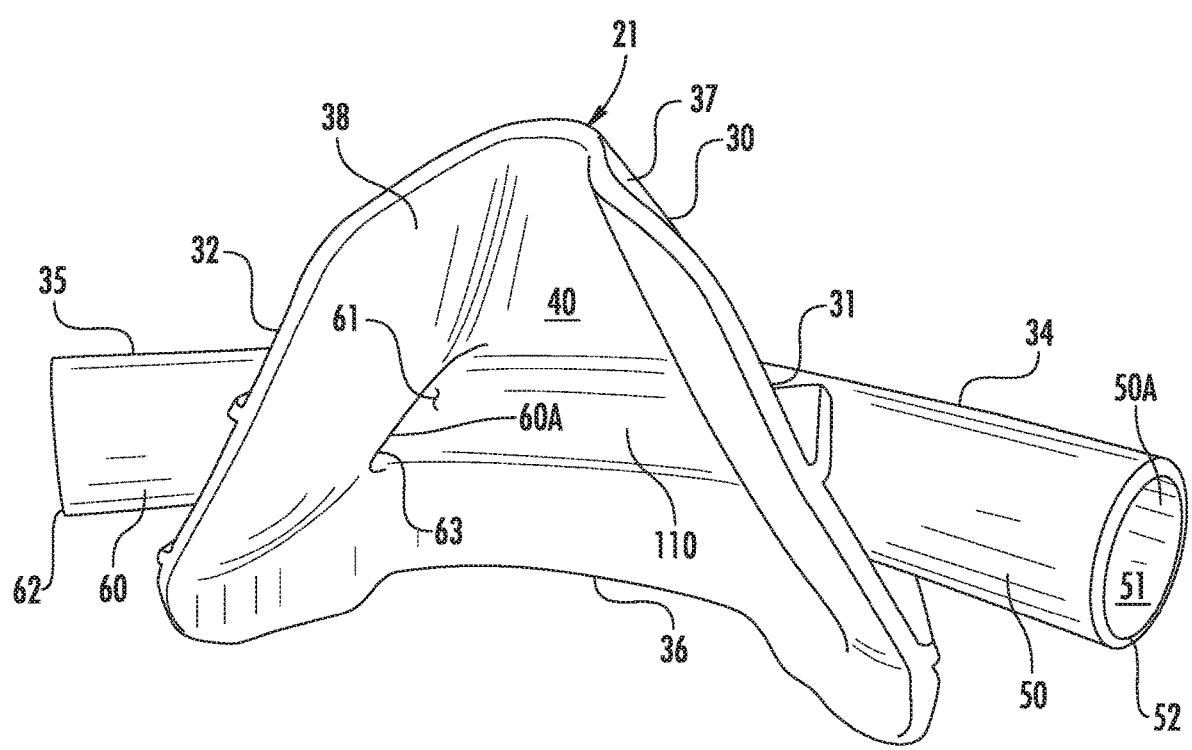
Figure 12:
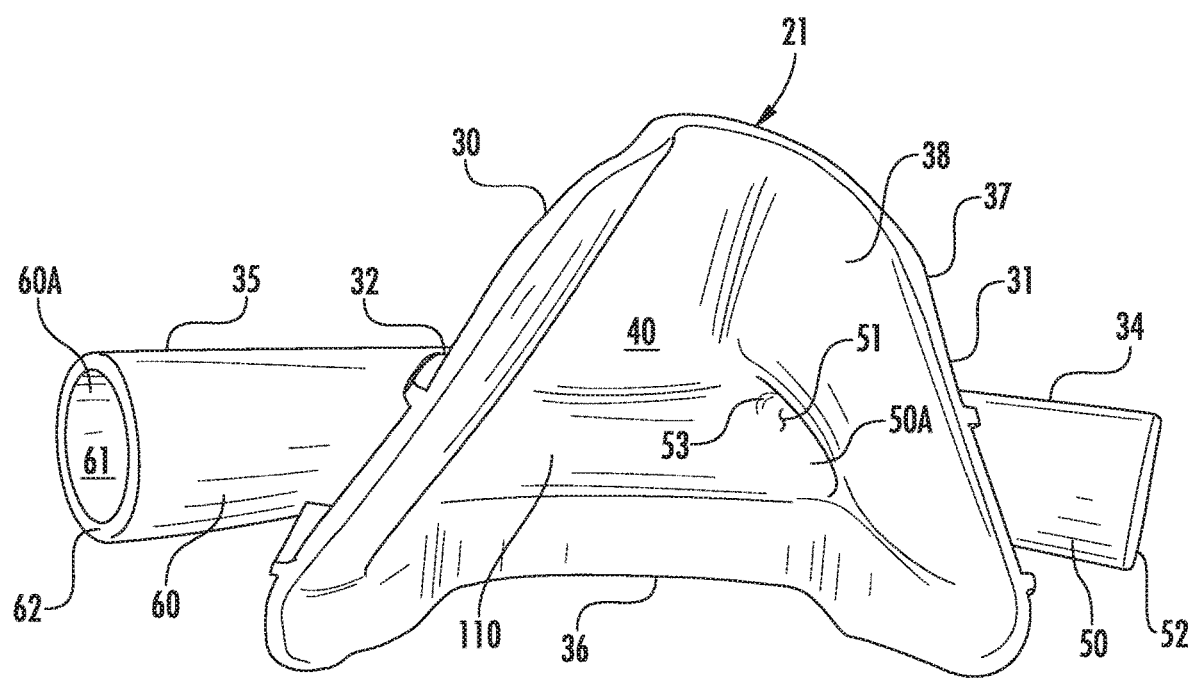
Figure 13:
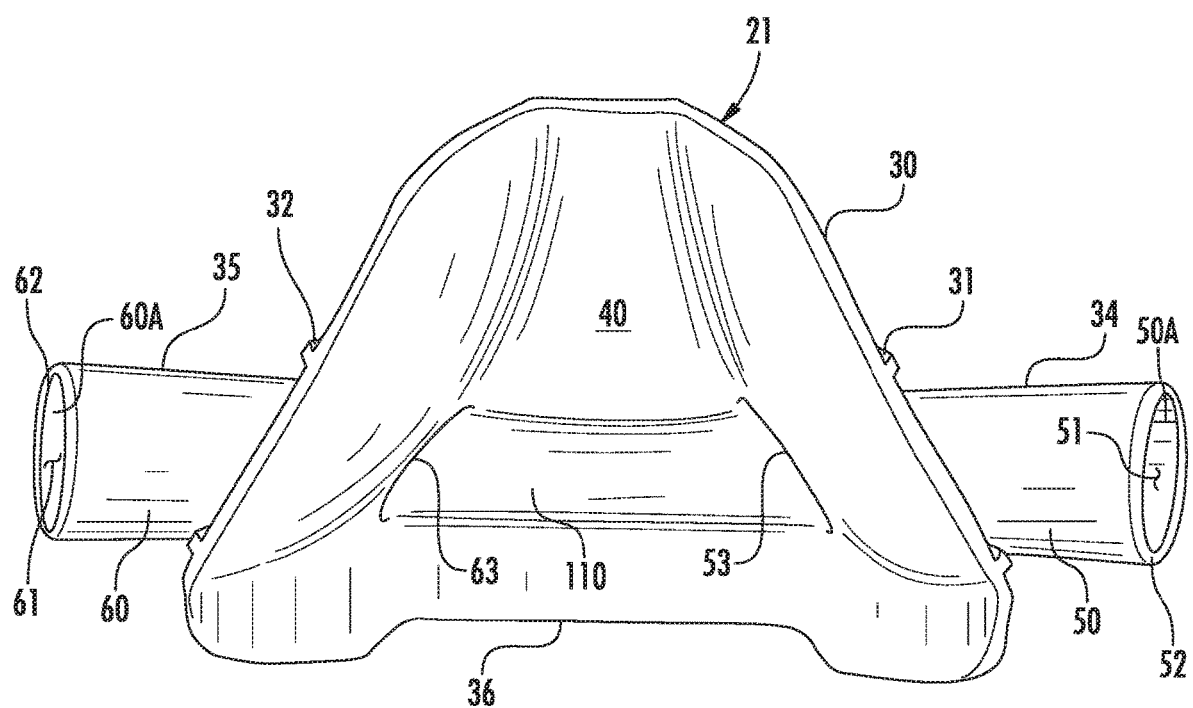

Connectors 80A and 80B are identical. In FIG. 4, connectors 80A and 80B each include a cylindrical body 81 having opposed ends 82 and 83 and a bore 84 extending therethrough from end 82 to end 83. End 82 of connector 80A is matingly and sealingly engagable within inlet 52 of inhalation member 34, and end 83 of connector 80A is matingly and sealingly engagable within outlet end 70A of delivery hose 70. End 82 of connector 80B is matingly and sealingly engagable within outlet 62 of exhalation member 35, and end 83 of connector 80B is matingly and sealingly engagable within inlet 72A of vacuum hose 72.

In FIGS. 1, 2, and 3, outlet end 70A of delivery hose 70 is connected to inlet 52 of cylindrical sidewall 50 of inhalation member 34 with connector 80A, and inlet end 72A of vacuum hose 72 is connected to outlet 62 of cylindrical sidewall 60 of exhalation member 35 with connector 80B, connector 80A is for admitting respirable gas into inhalation member 34, and connector 80B is for conducting exhaust gas from exhalation member 35. Delivery hose 70 extends from outlet end 70A coupled to inlet 52 of inhalation member 34 with connector 80A to gas source 71. Vacuum hose 72 extends from inlet end 72A coupled to outlet 62 of exhalation member 35 with connector 80B to vacuum source 73. In FIG. 1, scavenger valve 75 coupled to vacuum hose 72 is spaced apart from mask 21 and is between exhalation member 35 and vacuum source 73 at a location that is remote from mask 21.

In use, gas source 71 applies respirable gas to delivery hose 70, which conveys the respirable gas to inhalation member 34. Inhalation member 34, in turn, conveys the respirable gas from delivery hose 70 to body 30, specifically to interior 40 of body 30, for inhalation by a user. Upon exhalation by the user, exhalation member 35 conducts exhaled/exhaust gas from body 30, specifically from interior 40 of body 30, into vacuum hose 72. Vacuum source 73 pulls the exhaled/exhaust gas outwardly into vacuum hose 72 from exhalation member 35, and through vacuum hose 72 to scavenger valve 75, which exhausts the exhaled/exhaust gas therethrough from vacuum hose 72 to an atmosphere at the location of scavenger valve 75 that is remote from body 30. Scavenger valve 75 is a one-way valve, which enables the flow of exhaled/exhaust gas therethrough from vacuum hose 72 to the atmosphere, and disables gas flow therethrough into vacuum hose 72 from the atmosphere, and does not interfere with the ability of vacuum source 73 to maintain a vacuum in vacuum hose 73 for pulling the exhaled/exhaust gas outwardly into vacuum hose 72 from exhalation member 35, and through vacuum hose 72 to scavenger valve 75.

The location of scavenger valve 75 coupled to vacuum hose 72 at a location remote from body 30 enables scavenger valve 75 to exhaust or otherwise expel the exhaust gas from vacuum hose 72 to the atmosphere at the location of scavenger valve 75 that is remote from body 30, which disables the exhaust gas expelled from scavenger 75 from being inhaled by the dental or health professional when working on the teeth or other part of the facial area of the patient wearing mask 21, in accordance with the principle of the invention. The expulsion of the exhaust gas from vacuum hose 72 at scavenger valve 75 also disables the exhaust gas from being pulled into vacuum source 73.

Figure 14:
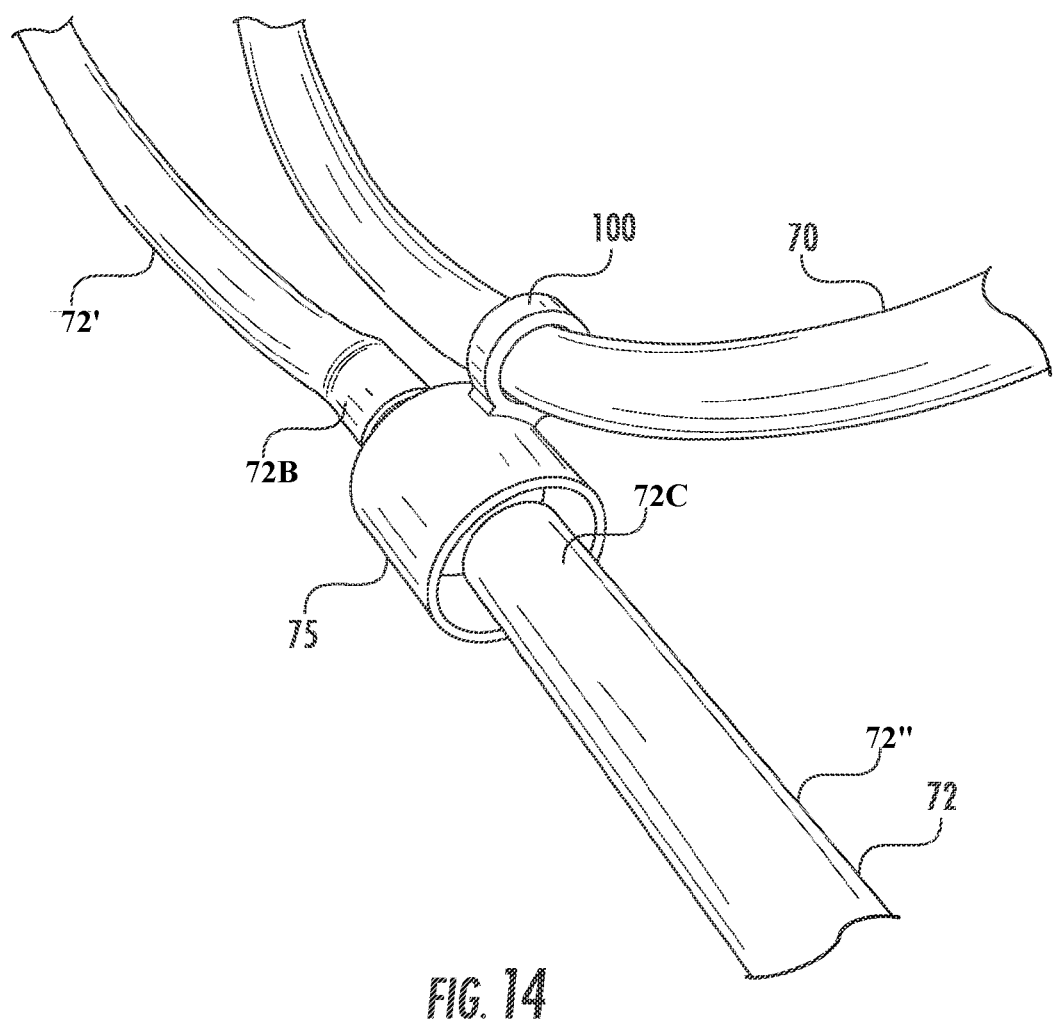
FIGS. 14 and 15 are fragmentary perspective views corresponding to FIG. 1, illustrating a coupling tying the delivery hose to the scavenger valve.
Figure 15:
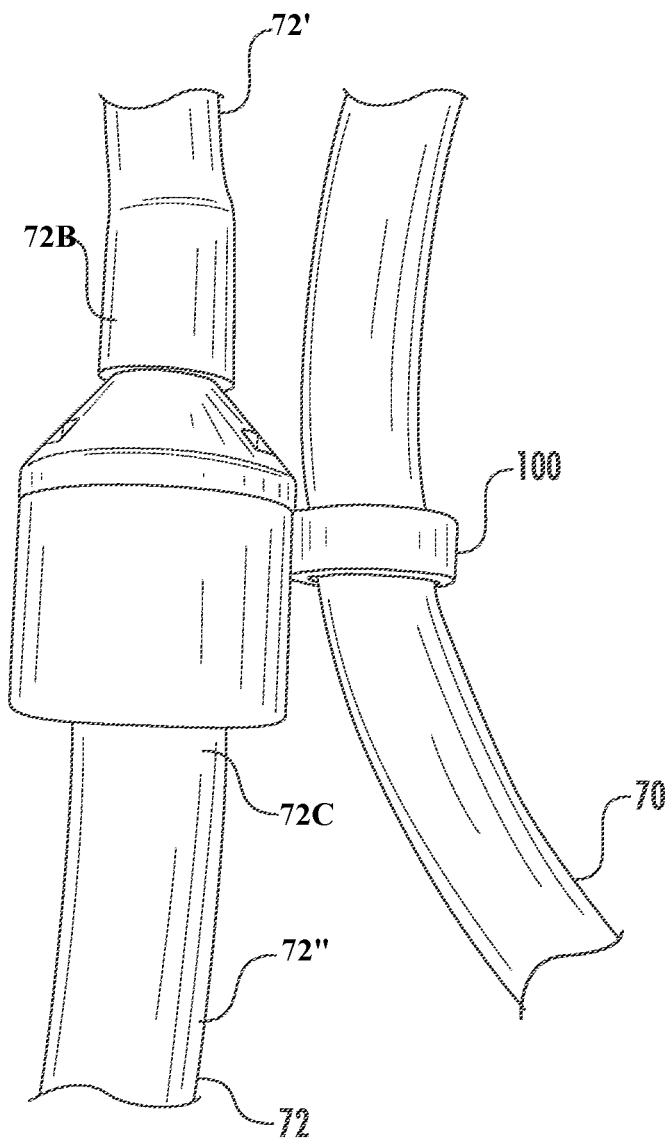
Figure 16:
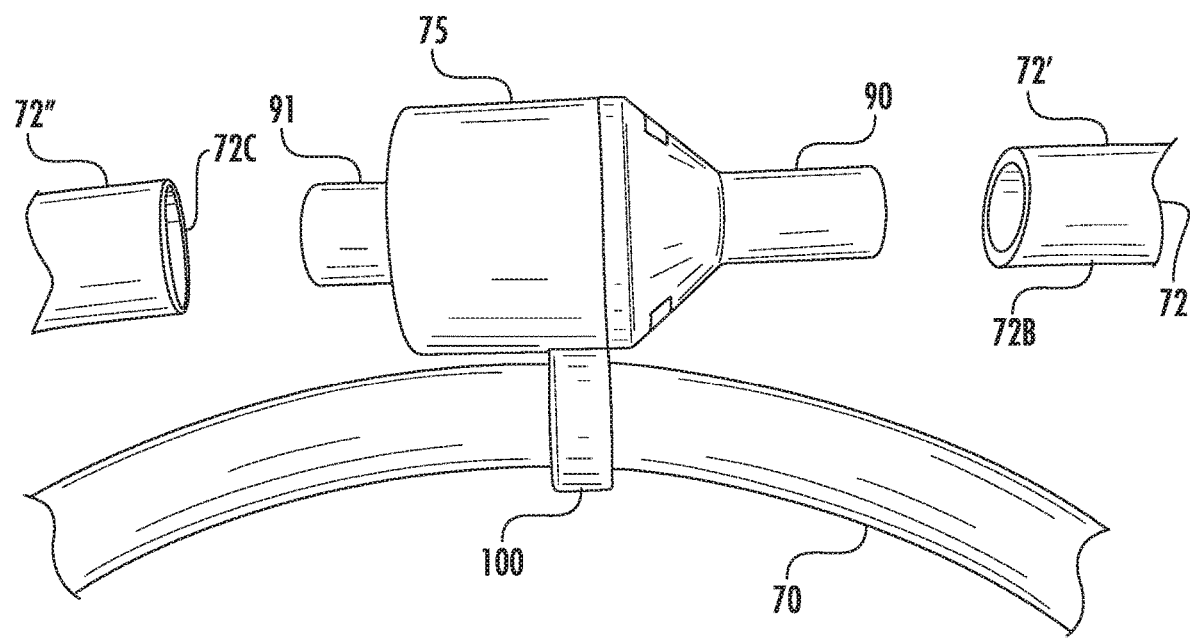
FIG. 16 is an exploded view corresponding to FIGS. 14 and 15.

In FIG. 1, vacuum hose 72 includes two hose components, namely, a proximal vacuum hose segment 72', and a distal vacuum hose segment 72". Proximal vacuum hose segment 72' extends from inlet end 72A coupled to outlet 62 of exhalation member 35 with connector 80B to outlet end 72B in FIGS. 1 and 14 coupled to scavenger valve 75, and distal vacuum hose segment 72" extends from an inlet end 72C coupled to scavenger valve 75 in FIGS. 1 and 14 to vacuum source 73 in FIG. 1. In FIG. 16, scavenger valve 75, which is a conventional scavenger valve, includes inlet end 90 and outlet end 91. Inlet end 90 of scavenger valve 75 is matingly and sealingly engagable within outlet end 72B of proximal vacuum hose segment 72', and outlet end 91 of scavenger valve 75 is matingly and sealingly engagable within inlet end 72C of distal vacuum hose segment 72".

And so proximal vacuum hose segment 72' extends from exhalation member 35 to scavenger valve 75, and distal vacuum hose segment 72" extends from scavenger valve 75 to vacuum source 73, in FIG. 1. Exhalation member 35 conducts exhaled/exhaust gas from body 30, specifically from interior 40 of body 30, into proximal vacuum hose segment 72'. Vacuum source 73 pulls the exhaled/exhaust gas outwardly into proximal vacuum hose segment 72' from exhalation member 35, and through proximal vacuum hose segment 72' to scavenger valve 75, which exhausts the exhaled/exhaust gas therethrough from proximal vacuum hose segment 72' to the atmosphere. Again, scavenger valve 75 is a one-way valve, which enables the flow of exhaled/exhaust gas therethrough from vacuum hose 72 to the atmosphere, and disables gas flow therethrough into proximal and distal vacuum hose segments 72' and 72" that form vacuum hose 72 from the atmosphere, and does not interfere with the ability of vacuum source 73 to maintain a vacuum in distal vacuum hose segment 72" and proximal vacuum hose segment 72'.

In FIGS. 1 and 14-16, scavenger valve 75 is coupled to delivery hose 70 with a collar 100, for tying/holding delivery hose 70 and vacuum hose together and for disabling delivery hose 70 and vacuum hose 72 from being pulled apart and scattering haphazardly apart from one another. Delivery hose 70 extends through collar 100, which is formed integrally with scavenger 75.

In FIGS. 9-13, inner surface 38 is formed with surface contour 110. Surface contour 110 is concave, being curved inwardly away from edge 36 at the rear of body 30 of mask 31 toward frontal midpoint 33, and defines a half pipe structure that is elongate and that extends transversely along body 30 from outlet 53 of inhalation member 34 in FIGS. 9, 12, and 13, across frontal midpoint 33 to inlet 63 of exhalation member 35 in FIGS. 10, 11, and 13. Surface contour 110 abuts inner surface 50A of cylindrical sidewall 50 of inhalation member 50 at outlet 53. Surface contour 110 abuts inner surface 60A of cylindrical sidewall 60 of exhalation member 60 at inlet 63. Furthermore, the inherent curvature of contour 100 corresponds to and abuts the inherent curvatures of the inner surfaces 50A and 60A of cylindrical sidewalls 50 and 60 at outlet 53 and inlet 63, respectively. As a result of this described structural arrangement between contour 110 and inner surfaces 50A and 60A of cylindrical sidewalls 50 and 60 and outlet 53 and inlet 63 as described, contour 110 cooperates with outlet 53 of inhalation member 34 in FIGS. 9, 12, and 13 to form a laminar flow of respirable gas from outlet 53 to interior 40, when respirable gas is applied to interior 40 from outlet 53 of inhalation member 34, and cooperates with inlet 52 of exhalation member 35 in FIGS. 10, 11, and 13 to form a laminar flow of exhaust gas from interior 40 to inlet 62, when exhaust gas is exhaled into interior 40. The laminar flow of respirable gas formed by contour 110 when the respirable gas enters interior 40 and interacts with contour 110 enables a laminar flow application of the respirable gas to the respiratory organ of a user in interior 40 focusing the respirable gas to the user's respiratory organ for ameliorating inhalation. The laminar flow of exhaust gas formed by contour 110 when the exhaust gas is exhaled into interior 40 when the user exhales through the respiratory organ and interacts with contour 110 enables a laminar flow application of the exhaust gas to inlet 63 of exhalation member 35 from interior 40 focusing the exhaust gas to inlet 63 to exhalation member 35 ameliorating the exhaust of the exhaust gas from interior 40 and into vacuum hose 72, in accordance with the invention.

The invention has been described above with reference to illustrative embodiments. However, those skilled in the art will recognize that changes and modifications may be made to the embodiments without departing from the nature and scope of the invention. Various changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

The invention claimed is:

1. An apparatus for administering a respirable gas to an individual, which individual includes a facial area containing a respiratory organ for receiving respirable gas and for expelling exhaust gas, and for scavenging exhaust gas from the individual, the apparatus comprising:
a body, the body is cup-shaped, includes a first side and a second side, and is receivable against the facial area for enclosing the respiratory organ, the body further includes an apex at a frontal midpoint of the body; an inhalation member extends from the first side of the body to the apex; an exhalation member extends from the second side of the body; a vacuum hose for coupling a vacuum source to the exhalation member; a scavenger valve coupled to the vacuum hose; the inhalation member for administering respirable gas into the body, the exhalation member for exhausting exhaust gas from the body into the vacuum hose, and the scavenger valve for exhausting exhaust gas therethrough from the vacuum hose to an atmosphere, wherein the exhalation member extends from the second side of the body to the apex such that the inhalation member and the exhalation member have a joint exterior surface at the apex that defines a half pipe structure that is elongate and that extends transversely along the body from the exhalation member to the inhalation member.

2. The apparatus according to claim 1, further comprising the scavenger valve for disabling gas flow therethrough into the vacuum hose from the atmosphere.

3. The apparatus according to claim 1, further comprising: the body includes an inner surface that defines an interior of body; the inhalation member further for administering respirable gas from an inlet of the inhalation member into the interior; the exhalation member further for exhausting exhaust gas through an inlet of the exhalation member from the interior to the vacuum hose; a concave surface contour in the inner surface of the body extends from an outlet of the inhalation member to the inlet of the exhalation member; the concave surface contour cooperates with the outlet of the inhalation member to form a laminar flow of respirable gas from the outlet of the inhalation member to the interior, when respirable gas is applied to the interior from the outlet of the inhalation member; and the concave surface contour cooperates with the inlet of the exhalation member to form a laminar flow of exhaust gas from the interior to the inlet of the exhalation member, when exhaust gas is exhaled into the interior.

4. The apparatus according to claim 1, wherein the body has a protruding surface adjacent to the inhalation member such that the protruding surface extends transversely along the first side of the body.

5. An apparatus for administering a respirable gas to an individual, which individual includes a facial area containing a respiratory organ for receiving respirable gas and for expelling exhaust gas, and for scavenging exhaust gas from the individual, the apparatus comprising:
a body, the body is cup-shaped, includes a first side and a second side, and is receivable against the facial area for enclosing the respiratory organ, the body further includes an apex at a frontal midpoint of the body; an inhalation member extends from the first side of the body to the apex; an exhalation member extends from the second side of the body; a vacuum hose coupling a vacuum source to the exhalation member; a scavenger valve coupled to the vacuum hose between the exhalation member and the vacuum source; the inhalation member for administering respirable gas into the body, the exhalation member for exhausting exhaust gas from the body into the vacuum hose, and the scavenger valve for exhausting exhaust gas therethrough from the vacuum hose to an atmosphere between the exhalation member and the vacuum source, wherein the exhalation member extends from the second side of the body to the apex such that the inhalation member and the exhalation member have a joint exterior surface at the apex that defines a half pipe structure that is elongate and that extends transversely along the body from the exhalation member to the inhalation member.

6. The apparatus according to claim 5, further comprising the scavenger valve for disabling gas flow therethrough into the vacuum hose from the atmosphere.

7. The apparatus according to claim 5, further comprising: the body includes an inner surface that defines an interior of body; the inhalation member further for administering respirable gas from an inlet of the inhalation member into the interior; the exhalation member further for exhausting exhaust gas through an inlet of the exhalation member from the interior to the vacuum hose; a concave surface contour in the inner surface of the body extends from an outlet of the inhalation member to the inlet of the exhalation member; the concave surface contour cooperates with the outlet of the inhalation member to form a laminar flow of respirable gas from the outlet of the inhalation member to the interior, when respirable gas is applied to the interior from the outlet of the inhalation member; and the concave surface contour cooperates with the inlet of the exhalation member to form a laminar flow of exhaust gas from the interior to the inlet of the exhalation member, when exhaust gas is exhaled into the interior.

8. An apparatus for administering a respirable gas to an individual, which individual includes a facial area containing a respiratory organ for receiving respirable gas and for expelling exhaust gas, and for scavenging exhaust gas from the individual, the apparatus comprising:

a body, the body is cup-shaped, includes a first side and a second side, and is receivable against the facial area for enclosing the respiratory organ, the body further includes an apex at a frontal midpoint of the body; an inhalation member extends from the first side of the body to the apex; an exhalation member extends from the second side of the body; a respirator circuit, the respirator circuit including a delivery hose coupling a gas source to the inhalation member, a vacuum hose coupling a vacuum source to the exhalation member, and a scavenger valve coupled to the vacuum hose between the exhalation member and the vacuum source, the delivery hose for delivering respirable gas from the gas source to the inhalation member, the inhalation member for administering respirable gas into the body, the exhalation member for exhausting exhaust gas from the body into the vacuum hose, and the scavenger valve for exhausting exhaust gas therethrough from the vacuum hose to an atmosphere between the exhalation member and the vacuum source, wherein the exhalation member extends from the second side of the body to the apex such that the inhalation member and the exhalation member have a joint exterior surface at the apex that defines a half pipe structure that is elongate and that extends transversely along the body from the exhalation member to the inhalation member.

9. The apparatus according to claim 8, further comprising the scavenger valve for disabling gas flow therethrough into the vacuum hose from the atmosphere.

10. The apparatus according to claim 8, further comprising: the body includes an inner surface that defines an interior of body; the inhalation member further for administering respirable gas from an inlet of the inhalation member into the interior; the exhalation member further for exhausting exhaust gas through an inlet of the exhalation member from the interior to the vacuum hose; a concave surface contour in the inner surface of the body extends from an outlet of the inhalation member to the inlet of the exhalation member; the concave surface contour cooperates with the outlet of the inhalation member to form a laminar flow of respirable gas from the outlet of the inhalation member to the interior, when respirable gas is applied to the interior from the outlet of the inhalation member; and the concave surface contour cooperates with the inlet of the exhalation member to form a laminar flow of exhaust gas from the interior to the inlet of the exhalation member, when exhaust gas is exhaled into the interior.

* * * * *